US009254187B2

(12) United States Patent
Sudekum

(10) Patent No.: US 9,254,187 B2
(45) Date of Patent: Feb. 9, 2016

(54) TERMINAL TISSUE ATTACHMENT AND REPAIR DEVICE

(71) Applicant: Anthony E. Sudekum, O'Fallon, MO (US)

(72) Inventor: Anthony E. Sudekum, O'Fallon, MO (US)

( * ) Notice: Subject to any disclaimer, the term of this patent is extended or adjusted under 35 U.S.C. 154(b) by 71 days.

(21) Appl. No.: 14/286,333

(22) Filed: May 23, 2014

(65) Prior Publication Data

US 2014/0257349 A1 Sep. 11, 2014

Related U.S. Application Data

(63) Continuation-in-part of application No. 13/946,607, filed on Jul. 19, 2013, now Pat. No. 9,149,354.

(60) Provisional application No. 61/915,574, filed on Dec. 13, 2013, provisional application No. 61/673,827, filed on Jul. 20, 2012.

(51) Int. Cl.
*A61F 2/08* (2006.01)
*A61B 1/06* (2006.01)
*A61F 2/00* (2006.01)
*A61B 17/06* (2006.01)

(52) U.S. Cl.
CPC ......... *A61F 2/0811* (2013.01); *A61B 17/06166* (2013.01); *A61F 2/0063* (2013.01); *A61F 2/08* (2013.01); *A61F 2002/087* (2013.01)

(58) Field of Classification Search
CPC . A61F 2/08; A61F 2/0811; A61F 2002/0817; A61F 17/1146
See application file for complete search history.

(56) References Cited

U.S. PATENT DOCUMENTS 6,143,029 A * 11/2000 Rippstein .................. A61F 2/08
602/36
2013/0060333 A1 * 3/2013 Gonzalez-Hernandez A61F 2/0811
623/13.15

* cited by examiner

*Primary Examiner* — Thomas J Sweet
*Assistant Examiner* — Daniel Bissing
(74) *Attorney, Agent, or Firm* — Charles McCloskey

(57) ABSTRACT

A terminal soft tissue attachment and repair device has a sheet of mesh with two longitudinal sides and two lateral ends angled to the sides. One end has a smooth surface where the healing tissue rests and the sides mutually overlap. The device attains a frusto-conical shape of a proximal component and a distal component. The two sides and one end of the proximal component have suture holes. The other end of the proximal component merges with both sides and joins them to the distal component. From the joint, the two sides extend in a V shape spanned by laced suture. A surgeon places an end of tissue within the device. The surgeon then laces suture and then pulls it from one location to secure the invention upon the tissue and the distal component to a bony insertion. The invention attains a shape like the natural tissue.

20 Claims, 8 Drawing Sheets

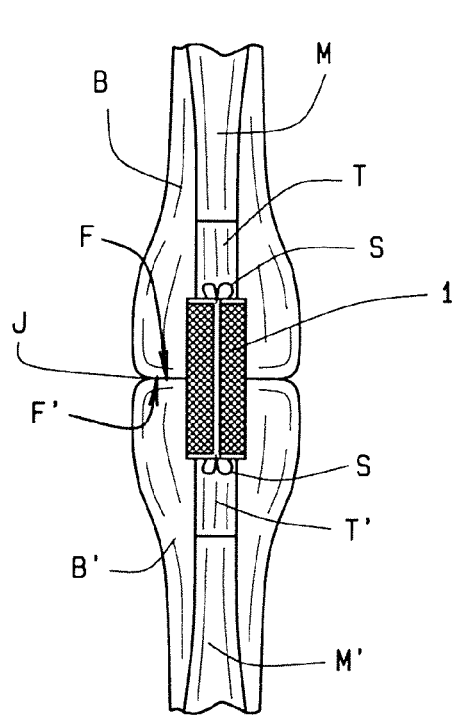
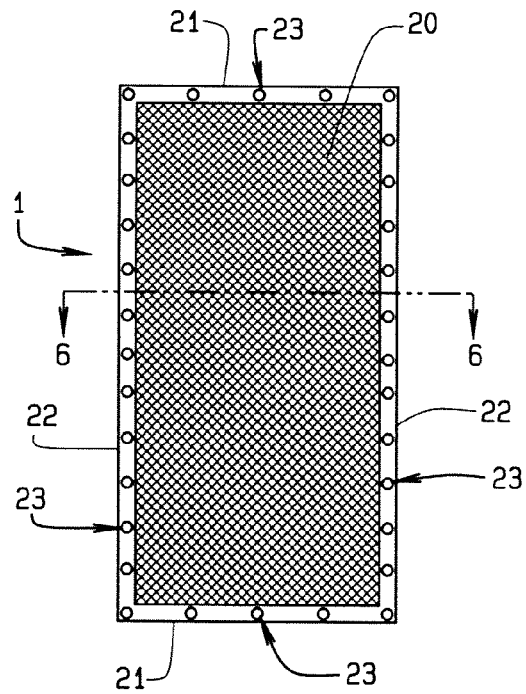
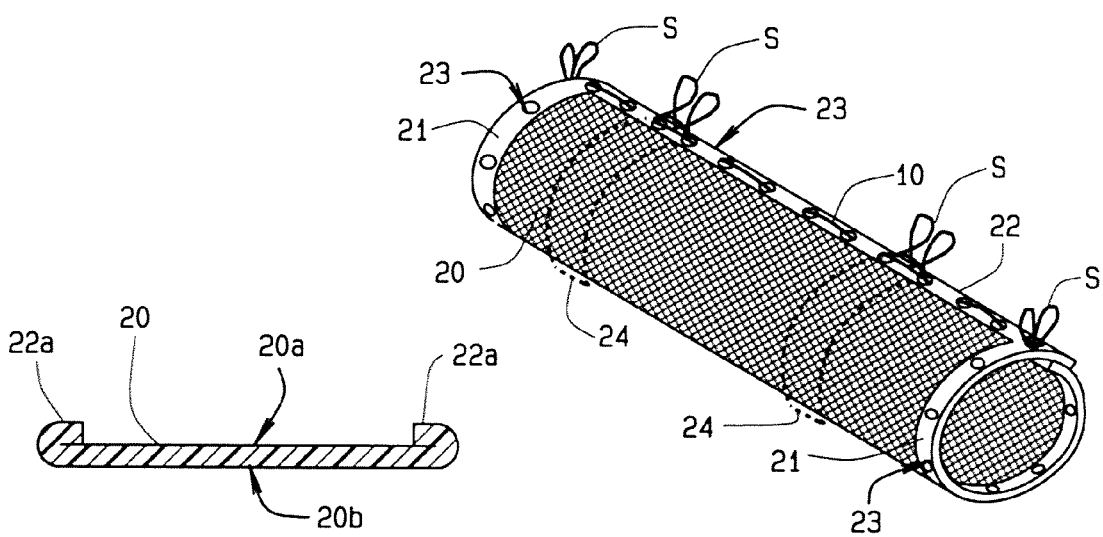
FIG. 4    FIG. 5
FIG. 6    FIG. 7

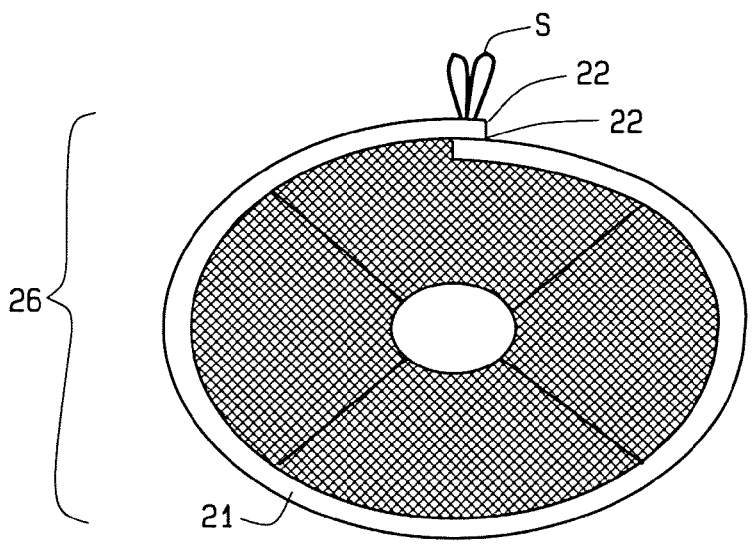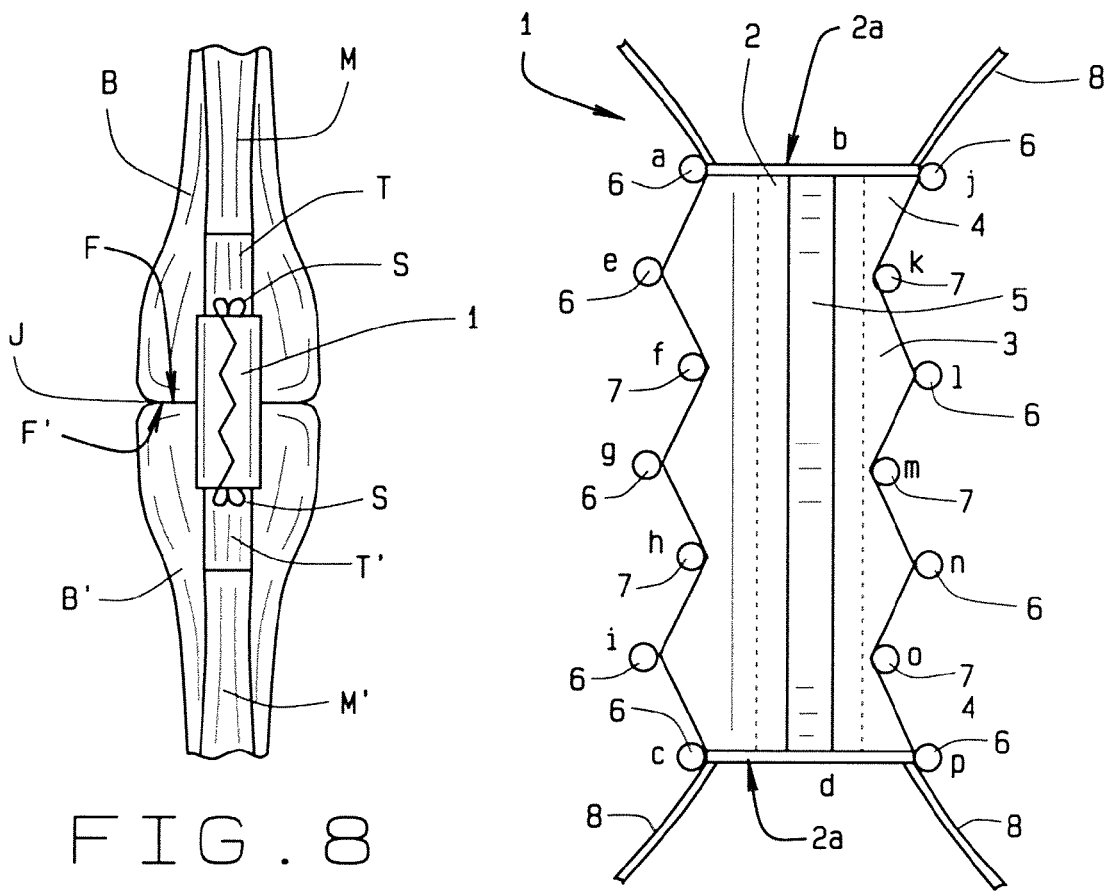

TERMINAL TISSUE ATTACHMENT AND REPAIR DEVICE

CROSS-REFERENCE TO RELATED APPLICATION

This non-provisional application claims priority to the provisional application 61/915,574 filed on Dec. 13, 2013, and the pending non-provisional application Ser. No. 13/946,607 filed on Jul. 19, 2013, and the provisional application 61/673,827 filed on Jul. 20, 2012, which are all owned by the same inventor.

BACKGROUND OF THE INVENTION

The terminal tissue attachment and repair device generally relates to orthopedic devices and more specifically to an elongated tissue enwrapping and repair device. More particularly, the invention wraps one end of an elongated tissue and secures that end to a bony insertion or fixed anatomic point.

Effective repair of elongated tissue, such as flexor tendons, extensor tendons, ligaments, muscles and the like, has long been a significant problem that remains unresolved within the realms of hand surgery, orthopedic surgery and reconstructive musculoskeletal surgery. The pursuit of a secure, relatively simple, inexpensive surgical technique and device to assist and facilitate the effective repair of tendons, ligaments and other elongated tissues, still eludes hand surgeons, orthopedic surgeons and the practice and advancement of musculoskeletal reconstructive surgery.

The problems which must be addressed in any tendon, ligament or elongated soft tissue repair technique and device include creation of a connection, co-aptation or union of the cut end(s) of the tendon or ligament to each other in the case of a mid-substance disruption or to the distal bony attachment in the case of a terminal tendon disruption. Though this specification refers often to tendons and flexor tendon, the invention may see use upon ligaments, muscles, nerve tissue, and the like.

Flexor tendons in the hands and feet pass through a relatively narrow "tunnel" of fibro-osseus tissue which extends from the metacarpophalangeal, or MP joint proximally to the distal interphalangeal, or DIP joint distally. Tendon movement through this tunnel is referred to as "tendon excursion". In the hand this region is known as "no man's land" and/or "zone 2" by orthopedic practitioners.

The term "no man's land" arose from early surgeons who indicated that primary repair of flexor tendons in this region of the hand could not be performed successfully. This pessimistic approach came about because the practitioners' experience of the repairs in this zone consistently failed due to adhesions and/or tendon rupture after repair. Because the results with primary flexor tendon repair were so dismal, hand surgeons avoided primary tendon repair and instead performed delayed secondary repairs with tendon grafting or performed no repairs of flexor tendons in this area at all.

When the tendon, ligament or elongated soft tissue is cut in its midsubstance and repair is performed, the two cut ends of the divided tissue are coapted, that is, held together and secured in this position using sutures or other tendon/ligament repair device. An end to end coaptation requires that enough tissue is available on either side of the laceration or rupture to facilitate "capture" and "purchase" of both ends of the ruptured soft tissue and securement with suture or other restraining material so that a secure union or coaptation between these two ends is established. Practitioners refer to this as an "end to end" repair of tendon, ligament or muscle.

In connecting the two ends, this typically involves passing sutures through both sides of the lacerated tendon and then tying the two free ends of the suture together, thereby reapproximating and holding the cut ends together. Various suturing techniques have been used including a variety of criss-cross patterns, looped sutures, locking sutures, and the like. A proper tendon repair must create a repair and connection between the two cut ends of the tendon strong enough to withstand the forces involved in muscle contraction, such as for finger, wrist, elbow, shoulder, knee or ankle movement. Many of the existing repair techniques for the treatment of tendon injuries involve the use of four, six, or eight suture strands which are passed through the tendon "core" to provide adequate purchase and "strength of repair." Because multiple strands of suture pass through the "core" of the tendon, this also brings about multiple knots to secure the sutures which are holding the cut tendon ends together. These suture knots, may be placed in between the two cut ends at the site of the coaptation or on the outside of the tendon, depending on the technique utilized. When the knots are placed between the two cut ends at the site of the coaptation, the "core" sutures and knots may actually serve to prevent direct contact between the two ends of the healing tissue and this separation may serve to impede the tendon's ability to heal and form a stable repair/union.

When tendons are repaired utilizing current techniques the repaired tendon and adjacent joints must be immobilized afterwards so that the repair can heal. As a result of the prolonged period of immobilization required after repair, adhesions invariably form between the repaired tendon and the surrounding tissue. When tendon adhesions occur, then "excursion," or movement of the repaired flexor tendon as it passes through the retinacular "pulley" system has significant inhibition or restriction. In repair techniques where the suture knots are placed on the outside of the repaired tendons, these knots may contact and catch on the fibrous pulleys of the retinacular system that surround the tendons, thereby impeding tendon excursion and joint motion. Knots on the outside of the tendon frequently become a source of irritation and adhesions often form between the suture knots and the surrounding soft tissues which limits tendon excursion and active motion of the affected joints.

When a tendon, ligament or musculo-tendinous unit is cut near a terminal end, either proximally near the origin or distally near the insertion, then there is typically not enough tissue on one side of the rupture to facilitate an "end to end" repair and the surgeon must repair a "terminal" end of a tendon or ligament back to bone or other fixed skeletal tissue. To accomplish this, the surgeon must capture the cut "terminal" end of the ruptured/lacerated tendon/soft tissue and then secure it to bone or other fixed skeletal tissues such as joint capsule. In previous techniques and previous art suture or other material is passed or woven through the midsubstance or "core" of the ruptured/lacerated soft tissue and then the free "distal" end or ends of the suture material (which has been passed through and emerges from the terminal end of the lacerated soft tissue) is then sutured together, attached to or passed through a bone tunnel and fixed to the bone, using a variety of "anchoring" techniques including simple sutures, bone anchors, interference screws, or buttons (external buttons outside the skin or internal, "endo" buttons).

As noted above, patients require a structurally sound and strong repair but at the same time, a repaired tendon must also be able to move relative to adjacent skeletal components (tendon excursion) early in the postoperative period in order to minimize adhesions and facilitate skeletal and/or joint movement an ultimate function.

Tendons move through anatomic "tunnels" of synovial tissue and/or through fibro osseous retinacular systems. Tendon movement through these areas is termed "tendon excursion." Medicine has learned that the sooner active movement of the repaired tendon begins after the repair, the better, as long as this movement does not weaken or compromise the repair. Unfortunately, when early active motion is attempted after using current techniques, this movement results and gapping occurs at the repair site which can lead to tendon rupture.

Movement and excursion of a repaired or tendon serves to prevent and/or minimize adhesions between the repaired tendon and the surrounding tissues and thereby maximizing tendon excursion and optimizing skeletal movement. Similar to the problems encountered with suture material interfering with movement and/or healing of an "end to end" tendon repair, the same problems may occur with a "terminal tendon repair" when the suture material physically interferes with healing between the tendons and bone and/or results in adhesions between the tendon and surrounding soft tissues, thereby compromising healing and/or joint motion.

While the strength of the repair may be addressed by utilization of stronger and more numerous suture strands, the prior art has overlooked the bulkiness of the repaired sutured tendon at the site of the coaptation. The prior art does not adequately address the essential need to reproduce the normal anatomic shape of tendon at the repair site. An anatomic shape of the tendon at the site of the repair minimizes friction, facilitating the passage of the repaired tendon through the adjacent soft tissue, thereby maximizing tendon excursion. The bulkiness at the repair site comes from fraying of the lacerated tendon ends, hydration and swelling of the cut ends after an injury, from knots on or within the repaired tendon, and secondary to bunching of the two tendon ends brought together, all of which prevent movement and excursion of the repaired flexor tendon and compromise the ultimate functional results. Multiple sutures and knots at the repair site, as well as the "accordion effect" associated with tendon re-approximation site all contribute to the "fat repair site" which severely limits excursion and ultimately results in a poor functional result. Tendon re-approximation or coaptation occurs where the two cut ends are drawn together so that the tendon ends are compressed longitudinally and "bunched." The end result is a bulky repair site where the repaired tendon has a significantly larger diameter than the normal anatomic state, and a more irregular non-anatomic shape than the natural tendon. This bulkiness at the repair site and the non-anatomic shape of the repaired tendon has a profound negative effect on the ability of the repaired flexor tendon to move through the flexor tendon retinaculum system. Decreased friction and increased excursion at the repair site will serve minimize stress forces on the repair construct thereby protecting the repair, enhancing blood flow and healing at the repair site and decreasing the chances of adhesions or disruption at the repair site.

Medicine has the goal of developing a device or technique for repair of tendon, ligament or elongated anatomic tissue which is strong enough to withstand early, or immediate, active movement of the tendon, finger, hand, wrist, elbow, knee. ankle or involved joint/extremity after the repair. When early active motion begins very soon after the repair, then the risk of tendon adhesions reduces significantly. However, as noted above, early active motion requires a strong repair to resist gapping and minimum friction between the repaired tissue at the site of the repair and the surrounding soft tissue, synovial tissue, fibro-osseous tunnel and/or retinacular pulley system, through which the repaired tendon must pass.

The repair technique must ideally reproduce the normal anatomic size and shape of the uninjured tendon at the site of the tendon coaptation. Frequently, excessive bulkiness at the repair site occurs due to poor repair technique, excessive suture material and bunching of the repaired tissue at the repair site due to the "accordion effect". Reproducing the normal anatomic size and shape of the tendon at the repair site by decreasing excessive bulkiness of the soft tendon repair will help prevent the tendon from getting "hung up," or adherent to the surrounding soft tissue, through which the tendon must pass.

The ideal tendon repair construct accomplishes these goals: 1) enough strength and structural integrity to withstand the forces of muscle contraction, preventing gapping at the repair site and allowing for early active motion immediately after the repair; 2) optimize healing, blood flow and vascularity between the repaired/reapproximated cut tendon ends (end to end repair) or between the tendon and bone (terminal tendon repair); and 3) reproduce or approximate the normal anatomic shape of the tendon at the repair interface which will minimize friction and allow for normal unimpeded tendon excursion through the retinacular tunnel and/or surrounding soft tissues which will also help facilitate immediate active motion after repair.

The ideal tendon repair construct would securely fix the ruptured tendon ends together (end to end repair) or tendon to bone (terminal tendon repair). The ideal repair construct must also optimize healing and vascularity/blood flow at the repair site, re-create normal anatomy, minimize friction and adhesions at the repair site and allow for active skeletal motion to begin immediately after the repair.

DESCRIPTION OF THE PRIOR ART

Over the years, physicians, technicians, and device makers have built and used various tendon repair devices and methods, particularly for the fingers of the human hand. There are many suture repair techniques and devices which have been used, proposed and/or developed which have attempted to address the structural, physical, anatomic, dynamic and a functional aspects of lacerated flexor tendons which must be considered to achieve consistently good functional results with flexor tendon repair techniques.

For centuries though, people have made and played with a Chinese finger trap. The finger trap works as follows. The tightening of the trap is simply a normal behavior of a cylindrical, helically wound braid, usually the common biaxial braid. Pulling the entire braid (axial traction) lengthens and narrows it. The length is gained by reducing the angle between the warp and weft threads at their crossing points, but this reduces the radial distance between opposing sides and hence the overall circumference. The more one pulls, the more the circumference shrinks, that is, the trap tightens.

Also, practitioners have used Prolene® sutures from Ethicon® of Johnson and Johnson® to perform various Thread-lift® procedures. These procedures have utilized sutures to suspend soft tissue into a more cosmetically pleasing appearance for a patient. These sutures have barbs upon their ends that embed into the soft tissues, securing the sutures against axial loads. These sutures then allow upward lifting of the tissue.

Practitioners have also put to use various Quill Sutures® of Surgical Specialties, Corp. of Vancouver, British Columbia, Canada. These sutures have a tip that includes a pattern of barbs spaced along the length of each suture. The barbs allow for one way installation and embedment of sutures into tissue.

These barbs reduce the need for and complexity of knots used by surgeons. These sutures then allow upward lifting of the tissue.

The prior art also includes helical anchors, usually of metal, threaded into the ends of a severed tendon. Two anchors are used for each tendon and connected using a wire. The surgeon pulls the tendon ends to a desired position and then fixes the wire at that length. This metallic tendon repair becomes a permanent part of the patient and has some risk of rejection or working outwardly from the tendon and interfering with the operation of the joint under repair. The prior art also has embedded spines that bridge the gap between severed tendon ends. The spine has two ends with spaced apart ribs that extend at an angle to the spine. Each end has ribs extending outwardly in opposite directions so that upon pulling of the tendon, the spine remains in place. The spine and its ribs allow for insertion into the tendon ends but not removal. The ribs allow for one way installation. Both the anchors and the spines allow for the tendon to regrow across the severance between the ends. Akin to the helical anchors, the spines insert deep into tendon tissue putting that tissue at risk for mechanical degradation.

The present invention overcomes the disadvantages of the prior art and provides a terminal soft tissue attachment and repair device generally of mesh that wraps and compresses a repaired elongated tissue, such as a tendon, tendon graft, ligament or muscle into an ovoid cross sectional shape which approximates the normal size and shape of the uninjured tendon or ligament. The cross section of the invention approximates the normal anatomic shape of a tendon, more particularly an elliptical cross section. The re-creating of the normal size and anatomic shape of the repaired tissue serves to facilitate that minimal friction occurs at the tendon repair site and the healing tendon moves freely and has maximum excursion lengthwise without impediment by the surrounding soft tissue, synovial tissue, fibro-osseous tunnel and/or retinacular pulley system, through which the tendon must pass. This invention allows a surgeon to secure the device to the terminal end of a ruptured tendon, or other elongated tissue, which has been severed or ruptured from a terminal end, where the tendon would normally insert into bone. This device also has a distal component that allows for secure attachment of the repaired tendon to its normal site of insertion on the bone. The present invention provides a device that provides secure, stable attachment for repair of a terminal tendon that reproduces the normal size and shape of the terminal tendon anatomy and supports the structure of a healing tendon with minimal increase in tendon volume proximate a constricting tendon tunnel. The present invention compresses the circumference of the tendon into an ovoid shape and has folded edges for a smoother interface between the healing tendon and the invention. The present invention also provides a means by which the tendon is both "captured" by the device securely and then the tendon is securely attached to a point of bony insertion by means of the device. The present invention accomplishes these goals of a strong, stable tendon, ligament, tendon graft or elongated soft tissue repair which approximates normal anatomy at the repair site and is capable of facilitating immediate active skeletal motion.

SUMMARY OF THE INVENTION

Generally, the terminal tissue attachment and repair device is composed of two distinct parts: the proximal component and the distal component. The proximal component is composed of either a resorbable mesh material or a non-resorbable mesh material which receives and holds a free end of a patient's tendon or other elongated tissue. The proximal component has a generally conical shape with an open longitudinal slit of an elongated tapered V shape which extends for the length of the proximal component.

The distal component of the device is composed of a suture or woven fibrous material firmly attached to the proximal component. The distal component is smaller and narrower dimension than the proximal component. The distal component has a firm secure attachment to a tapered terminal end of the proximal component through adhesion, welding, weaving, mechanical connection and the like. The distal component serves as means of fixation and/or anchorage for the device so that the tendon, tendon graft, ligament or other elongated body tissue can be securely fixed to bone, such as a bony insertion or a skeletal point, or other rigid tissue.

The distal component serves to facilitate fixation of the proximal component of the device with the attached tendon, to bone or skeletal component. The suture or woven fibrous material ("tail" or "tails") which makes up the distal end of the device is fixed to the bone or skeletal component by passing the tails through the bone and knotting them together or used in conjunction with suture anchors, interference screws, buttons and like means to provide secure, permanent fixation of the device and attached tendon or other elongated body tissue to bone.

The present invention includes alternate embodiments for the distal end of the device depending on the type of procedure performed and means of distal fixation. The distal component of the device may be composed of either one or multiple woven suture strands, ribbons or "tails" that are confluent and attach to the proximal components. The distal component will be utilized to secure attachment of the device and contained soft tissue and proximal component to the bone or skeletal point of attachment.

The single or multiple tail embodiments for the distal component of the device could be utilized when the means of fixation utilizes a terminal interference screw embedded in bone to provide a terminal fixation and securement of the device and repaired tissue. The single tail or multiple tail variations may be utilized in conjunction with a terminal interference screw technique and may be utilized in a variety of reconstructive procedures, including but not limited to, flexor tendon repair, extensor tendon repair, distal bicep tendon repair, distal Achilles tendon repair, tendon graft reconstruction, anterior cruciate ligament/ACL (knee) reconstruction, elbow medial collateral ligament repair (Tommy John surgery), and the like.

For a terminal flexor or extensor tendon repair where the device is sutured directly to a point of attachment or when an external or internal button is utilized for distal fixation, then a double or multiple tail device would be most appropriate as later shown in FIG. 23.

The proximal component is composed of a sheet of mesh material generally having an isosceles trapezoid shape with two longitudinal sides, and two lateral ends at an angle to the longitudinal sides. The sheet further has a generally trapezoidal shape in flat form, as later shown in FIG. 22. The circumferential sheet mesh material on the outside of the tendon does not interfere with or impede circulation through the core of the tendon and allows for passage of fluids and gases present in healing tissue. The two lateral ends of the trapezoid are mutually parallel and spaced apart. The two longitudinal sides of the trapezoid are not parallel and attain an included angle. The wide end of the proximal component and the two sides also folds inwardly which presents smooth surfaces upon which the healing elongated tissue, such as a tendon, rests and where the sheet mutually joins upon enwrapping the healing tissue. When assembled, this unilateral closure device attains a somewhat conical shape and tapered open V shaped slit with the narrow portion of the slit oriented distally and the wider end of the conical shape being oriented proximally. The edges of the device are smooth to provide intimate contact of the device with the enwrapped tendon and without causing additional abrasion and laceration. These smooth edges closely approximate normal tendon contour and anatomy at the repair site. This construction including the intimate contact between the device and the tendon, approximates and reestablishes normal tendon shape and contour, optimizes blood flow at the repair site and also serves to minimize friction of the repaired tendon and invention against surrounding tissues, thereby optimizing healing and maximizing excursion/movement of the repaired tendon. The two longitudinal sides of the slit include a plurality of holes that admit suture material. The proximal component of the invention, which includes the mesh cylinder or cone with longitudinal slit, gently constricts in diameter as both sides, or wings, of the proximal component with contained tendon, approach mutual contact by way of tightening the laced sutures where the sutures provide circumferential consolidation or cerclage. The proximal component of the device tapers and becomes more narrow as it approaches and makes contact with the distal portion of the invention. The distal end of the invention composed of a woven or monofilament suture type material, may be a distal extension and compressed confluence of the material used in the proximal component the invention. The distal end of the invention is used to secure the invention along with the contained tendon, or elongated soft tissue, to a distal point of bony or joint attachment.

A surgeon, during use of the invention, places the end of healing elongated tissue, such as a severed tendon, inside, that is, within the proximal component of the invention through the wider end of the conical shape and advances the tendon distally to the tapered tip of the proximal component. Upon containing the tendon within the proximal component, the surgeon then laces the suture material through the plurality of holes on either side of the slit and pulls the ends of the suture material simultaneously, similar to tightening a shoelace, to compress and to constrict the mesh material upon and around the elongated tissue for securement of the invention and for healing of the tissue. Upon pulling the suture, the surgeon secures it using a knot. Alternatively, the surgeon laces the sides of the slit before inserting the elongated tissue into the invention. Having used the invention which is compressed circumferentially around the elongated tissue, the surgeon then places additional transfixion mattress sutures through the invention and also through the tendon, perpendicular to the long axis of the tendon and the invention to further secure the tendon to the invention. The transfixion sutures provide secure anchorage of the proximal component of the invention to the tendon and also compress the device along its anterior/posterior dimension. This compression further reestablishes the normal anatomic shape and form of a repaired tendon or other elongated tissue. The unilateral closure device with its mesh attains a generally ovoid, or elliptic or elliptical, shape that approximates the natural cross section of a tendon.

There has thus been outlined, rather broadly, the more important features of the invention in order that the detailed description thereof that follows may be better understood and that the present contribution to the art may be better appreciated. The present invention also includes additional sections of barbs at alternative orientations, undulating longitudinal edges for merging to sides of the invention, sutures placed within the lateral edges and the longitudinal edges, and loops extending outwardly from an edge for additional mechanical securement. Though this description refers to a tendon in many places, the invention may see use upon ligaments, muscles, nerves, and other slender, elongated body parts, that is, tissues, of people and select animals. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the present invention is to provide a terminal tissue attachment and repair device specifically designed to repair ruptures or lacerations at or near the distal, or terminal end of a tendon or elongated soft tissue whereby the device closes around and secures the tendon to the device on one end only while the other, distal end, of the invention is used to secure the invention and contained soft tissue to a point of bony attachment.

Another object is to provide such a terminal tissue attachment and repair device that allows for passage of the invention installed upon tissue, through the adjacent bony tunnel to facilitate secure attachment of the device and tendon to the distal bony insertion.

Another object is to provide such a terminal tissue attachment and repair device that a surgeon may install with a minimum of equipment.

Another object is to provide such a terminal tissue attachment and repair device that minimized the instance of bone grafting.

Another object is to provide such a terminal tissue attachment and repair device that cabins bone parts for receiving suture.

The terminal tissue attachment and repair device described in this application reaches the goals of 1) withstanding the forces of muscle contraction early active motion immediately after the repair; 2) optimizing healing, blood flow and vascularity between the repaired tendon ends or between the tendon and bone; and 3) approximating the normal anatomic shape of the tendon at the repair interface.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings,

FIG. 4 shows a bottom view, that is, palmar, of a finger joint with the present invention installed on a flexor tendon or alternatively a top view, that is, dorsal, of a finger joint with the present invention installed on an extensor tendon;

FIG. 5 shows a top view of the present invention;

FIG. 6 illustrates a bottom view of the present invention;

FIG. 7 provides an isometric view of the invention rolled;

FIG. 7a provides an end view of the invention;

FIG. 8 shows a top view of an alternate embodiment of the present invention;

FIG. 9 illustrates a bottom view of an alternate embodiment of the present invention;

The same reference numerals refer to the same parts throughout the various figures.

DESCRIPTION OF THE PREFERRED EMBODIMENT

Figure 1:
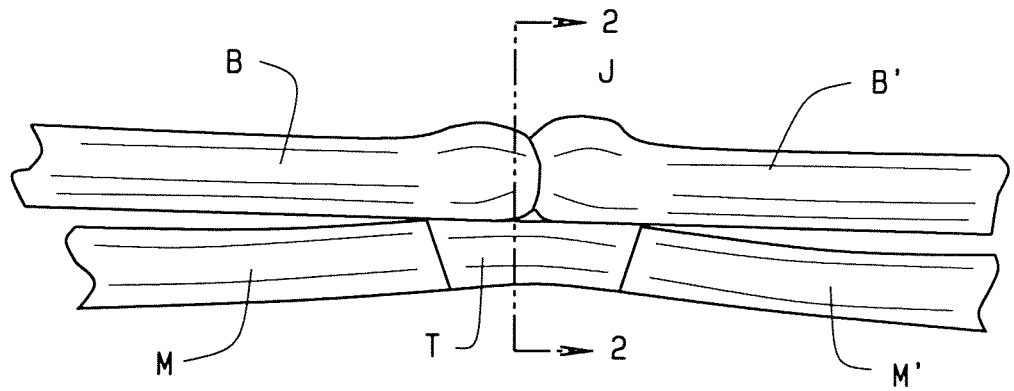
FIG. 1 provides a side view of a finger joint, including bony and tendon elements in longitudinal section.

The present invention overcomes the prior art limitations by providing a terminal tissue attachment and repair device also suitable for use upon other elongated body tissue such as ligaments, nerves, and the like. The "Tendon Trap," "Finger Trap," or tendon repair device is composed of a resorbable or non-absorbable suture material. The invention has a construction of a diagonal crisscrossing, interlocked sheet of mesh like construction which has the overall shape of an open or slit cylinder, or alternatively a conical shape. The longitudinal slit in the mesh cylinder or cone has a longitudinal opening to allow the tendon end(s) to be easily placed within the cylinder, whether the tendon has already been approximated or the cut ends remain unattached. The cylinder thus formed is generally hollow and the device attains an overall tubular form.

The grossly approximated tendon is then placed inside the open "Tendon Trap" cylinder or cone which wraps around and envelops the tendon repair site. For a standard finger tendon the "Tendon Trap" extends and enwraps at least 1 cm of tendon in order to provide adequate contact, purchase and securement of the device to the tendon. In the case of an end to end repair the tendon trap should extend and enwrap at least 1 cm of tendon on either end, measured from the repair/coaptation site.

Multiple interlocking closed loops line both sides of the open longitudinal slit. Two double-ended sutures with tapered curved needles on either end are passed back and forth from one side of the slit to the other through the closed loops on either side, advancing distally with each pass, much like lacing a shoe, and then tying the laces on both ends. The sutures have sufficient strength to withstand and to carry the load of a tendon, ligament, or other body part placed into the invention. The sutures also resist separation of the ends of the body part when in motion and placed into the invention. This construct will be used to "cinch" and tighten the tendon trap mesh around the tendon repair site as well as at least one cm proximal and distal (as with a girdle around the waist or tennis shoe around the foot).

As the "free ends" (with still attached curved needles, or sutures) are tightened, the tendon is compressed at the site of the repair and then the free ends are knotted at either end. The compression at the site of the tendon repair is an essential element. The attached needles can then be passed transversely, that is, perpendicularly through the tendon, back and forth at least once on each cut end of the tendon, possibly more passes, depending on the location and tendon type. This weaving of the tendon suture transversely through the tendon trap device, as well as through the tendon core, serves to secure and attach the tendon trap device to both ends of the cut tendon while at the same time compressing the tendon repair in the anterior-posterior, or AP, plane. This AP compression more closely approximates the natural, or normal, tendon demeanor, that is, design, which will greatly facilitate excursion of the repaired tendon through the retinacular system. The initial "holding suture" can then be removed if so desired or left in place if so desired, such that there will be no actual tendon which crosses through the "core" of the tendon at the site of the tendon coaptation. Elimination of the primary core suture serves to minimize any interference of the natural healing which must occur at the site of coaptation. The present invention provides a strong mesh netting of interlocking sutures on the outside of the tendon surface, while the multiple transverse core sutures which also pass through the mesh serve to compress and taper the repaired tendon in such a way that maximum excursion and early active motion is feasible.

The name "Tendon Trap" is derived from a child's toy called the "Chinese finger trap" which is a cylinder of woven interlocking diagonal woven material, which when placed around one finger on each hand "traps" the fingers and thus the hands together, in such a way that any attempt to pull the fingers out only tightens the trap around the fingers. This feature of the finger trap design incorporates within the design of the present invention, which is the quality of tightening of the cylinder around the tendon whenever axial longitudinal force, is applied to either end. This feature serves to tighten the invention around the repaired tendon whenever any load or force is transmitted to it. Compression of the tendon at the repair site repair will further stabilize the repair and facilitate improved tendon excursion by narrowing the caliber of the repair site.

The tendon repair device could be adapted for effective use in any part of the human body and can be utilized for repair and/or attachment of tendons, ligaments or other elongated body tissues. Though this description refers often to tendons and flexor tendon, the invention may see use upon ligaments and possibly upon nerve tissue. The size of the tendon trap may vary depending on the specific tendon and anatomic location of its use, however at least 1 cm proximal and 1 cm distal to the site of the injury would be required for finger flexor tendon repair. The Applicant foresees that the smallest longitudinal size would be approximately 2 cm and a largest size of approximately 8 cm to 10 cm for anterior cruciate ligament (ACL), biceps, triceps or Achilles tendon repair. The tendon trap mesh would be a custom designed mesh product manufactured in various sizes as "open lace-able cylinders." Ideally these cylinders would "hold their shape" to facilitate ease of application but all would tighten around and conform intimately and reproduce normal anatomy to the tendon or ligament once applied.

Figure 2:
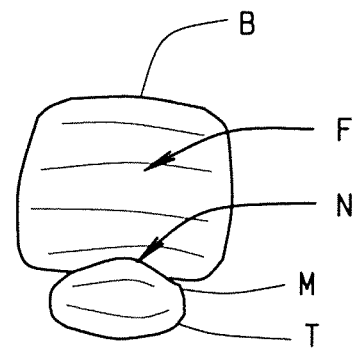
FIG. 2 shows a sectional view through a finger joint including bony and tendon elements in transverse section.
Figure 3:
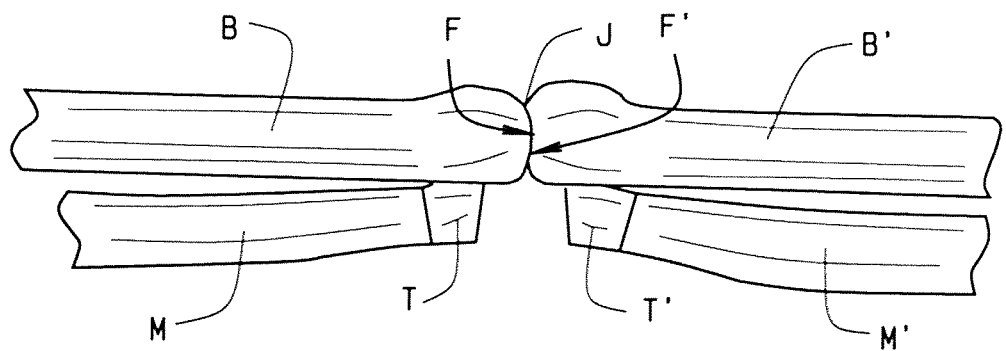
FIG. 3 shows a side view of a finger joint with the tendon severed in transverse section.

FIG. 1 shows a typical finger joint, as at a knuckle J. The knuckle is shown, the Applicant foresees application of this invention to other body parts, extremities and joints and skeletal structures that involve tendons, ligaments, muscles or nerves. Here shown in the joint, two bones, B, B' appear collinear but have a common joint to allow for angulation. The angulation of one bone relative to the other bone occurs upon operation of adjacent tendon T under the action of its connecting muscle M, M'. To allow for lever action across the joint and bone movement, the tendon extends across the joint through a tunnel N as shown in FIG. 2. The tunnel appears upon the face F of the bone B. The tunnel receives a portion of the thickness of the tendon and allows for passage of the tendon across the joint during movement. The tendon has a generally oval cross section that extends outwardly from the tunnel. However, as described above, a tendon may sever due to an injury or other cause as shown in FIG. 3. Upon severing, the tendon separates into two ends, T, T', as the connecting muscles contract. Once separated, the tendon ends T, T' can no longer operate the joint.

FIG. 4 then shows the present invention 1 installed upon a tendon T, T' undergoing repair. The present invention receives the ends T, T' into each end of the device and a surgeon secures the device to each tendon end using a transfixion stitch S. The surgeon then closes the device around the tendon and upon itself where the surgeon then stitches it closed. The stitches S and the operation of the invention keep it upon the tendon as the tendon ends heal and naturally reconnect.

The invention 1 appears in flat form from the top in FIG. 5. The invention has a generally planar rectangular form with a mesh construction as at 20. The planar form is its first position and the invention generally ships to customers in flat form or the first position. The invention has two mutually parallel and spaced apart lateral ends 21 and two mutually parallel and spaced apart longitudinal sides 22. The lateral ends are perpendicular to the longitudinal sides. Both the lateral ends and the longitudinal sides have a plurality of apertures 23 formed therein. The apertures may be arranged in a pattern. The apertures receive sutures during installation of the invention upon a tendon. The sutures pass through the apertures of both sides and mutually connect both sides similar to lacing upon a shoe. In an alternate embodiment, the apertures include grommets, one grommet per aperture, to reinforce the lateral edge at a puncture. In a further alternate embodiment, the longitudinal sides 22 have reinforcement, such as by folding over or by piping joined to the mesh layer. Also, in another alternate embodiment, the lateral ends 21 have reinforcement too, such as by folding over or by piping joined to the mesh layer.

FIG. 6 shows a sectional view transversely that reveals the construction of the two longitudinal sides 22. This view can also represent the construction of the lateral ends as well. The longitudinal sides are formed by folding a portion of the sheet of mesh material or construction, as at 20 inwardly. The portion is approximately 150% to 400% of the thickness of the material of the invention. The invention has an inner surface 20a that abuts a tendon upon installation and an opposite outer surface 20b that remains outwardly from the tendon. The invention has the folded portions 22a generally upon the inner surface as shown.

Having described the preferred embodiment, FIG. 7 has a surgeon placing it beneath the two severed ends T, T' and inserting the ends approximately 1 centimeter inwardly upon the device, not shown for clarity. The surgeon secures the alternate embodiment of the device to each end of the tendon with a transfixion stitch and then rolls each side 22 of the device upwardly and around the two ends T, T'—of a body part such as a tendon—attaining the cylindrical like form shown in FIG. 7. This form has an ovoid or elliptic shape in cross section and denotes the second position of the invention. The ovoid or elliptic cross section of the invention approximates the natural shape of a tendon or other body part placed into the invention. The ovoid shape has a major axis, or width, to minor axis, or height, of approximately 2.5 to 1, such as in an elliptic cylinder. The surgeon overlaps one longitudinal side 22 over the other side so that they are spaced apart but mutually parallel, such as in an overlapping joint. The surgeon also aligns the overlapped lateral ends 21 so that the lateral ends have a smooth texture transverse the tendon. The surgeon then extends a doubled suture, as at 10, through the apertures 23 along the overlapped sides 22. The surgeon does this suture from both ends 21 of the invention and secures it with a stitch S. The surgeon also performs an additional suture through the mesh of the invention as at 20 and into each cut end of the tendon as at 24 secured with a stitch S. These two sutures through the tendon mechanically connect the tendon repair to the mesh of the invention. With both ends sutured, the surgeon then pulls the sutures snug which closes the left side upon the right side of the invention generally above the tendon, not shown for clarity. The surgeon then takes another double suture and passes it through the apertures 23 along the lateral ends in a generally circular manner and pulls this other double suture and in doing so compresses the material of the device upon the tendon ends therein, or other body parts.

FIG. 7a provides an end view of the invention after installation upon the ends, T, T', of a tendon. The installation wraps the sides 22 upwardly and inwardly upon the tendon for securement in an overlap of the sides with a stitch S as shown. The invention attains an ovoid shape with a major axis, or width, as shown at 25, and a minor axis, or height, as shown at 26. The width is generally perpendicular to the height. The width has a ratio to the height of approximately 2.5 to 1. The ovoid cross section of the installed invention matches the typical tendon cross section. The sides 22 overlap generally centered upon the width of the invention shown on end and upon the minor axis of the cross section, that is, the top. The invention includes a material with a shape memory, with the shape of the tendon cross section imposed upon the material. Though having a shape memory, the invention permits compression and unfolding into flat form for shipping.

FIG. 8 then shows an alternate embodiment of the present invention 1 installed upon a tendon T, T' undergoing repair. The alternate embodiment receives the ends T, T' into each end of the device and a surgeon secures the device to each tendon end using a transfixion stitch S. The stitches S and the operation of the invention keep it upon the tendon as the tendon ends heal and naturally reconnect.

To reach the result shown in FIG. 8, the alternate embodiment of the invention begins in flat form shown in FIG. 9. The invention 1 has a generally flat form of mesh like material with two mutually parallel and spaced apart lateral ends 2, 2a, and two spaced apart opposed undulating sides. Each lateral end contains a reinforced tube like member the receives a suture 8. The undulating sides have a more rectilinear wave like form. The left side in the drawing has three flaps 3 of triangular shape while the right side in the drawing has two flaps 2 also of triangular shape offset half the length of a flap from the left side. The right side includes two half flaps 4, each locating proximate and end 2, 2a. The left side is denoted by the letters a, e, f, g, h, 1, c and the right side is denoted by the letters j, k, 1, m, n, o, p. The left side also includes outloops 6 shown at points a, e, g, 1, c and inloops 7 shown at points f, h. The inloops occupy an interior angle between two flaps. Then upon the right side, it includes outloops 6 shown at points j, l, n, p and inloops 7 shown at points k, m, o. The flaps of the left side mate between adjacent flaps upon the right side upon rolling the device as later shown. The device includes a backer 2 generally extending lengthwise between the left side and the right side as shown. The backer extends between points b, d.

Figure 10:
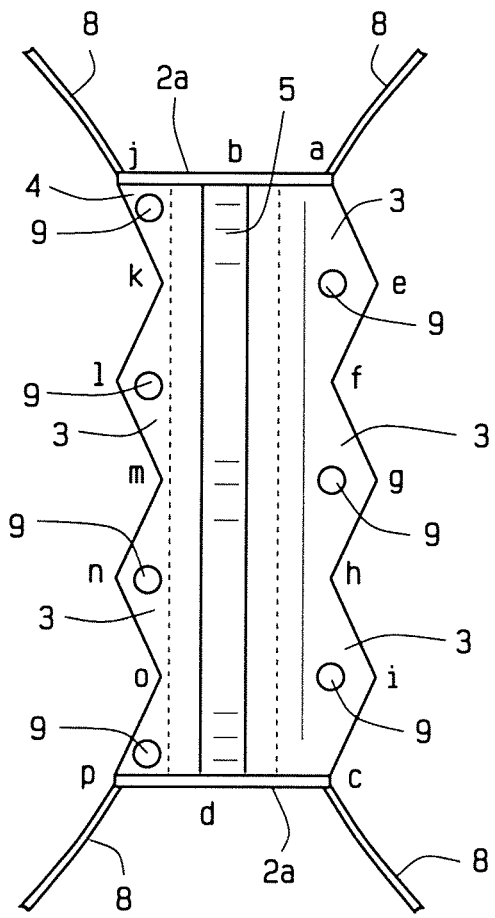
FIG. 10 illustrates a top view of an alternate embodiment of the present invention.

Turning the device over, FIG. 10 shows a bottom view of the device when in flat form. This view has the undulating patterns of each side reversed from FIG. 8. This view also shows that each flap, on both sides, includes an aperture 9. Each end 2, 2a also includes an aperture spaced outwardly from the backer towards a half flap 4. The apertures are generally inline with the outloops of the adjacent flap.

Figure 11:
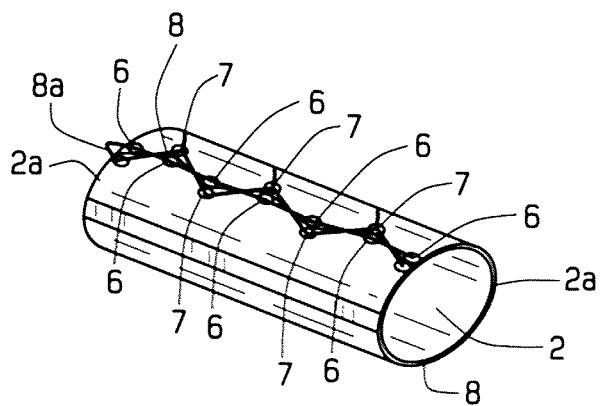
FIG. 11 provides an isometric view of an alternate embodiment of the invention rolled.

Having described the device, a surgeon places it beneath the two severed ends T, T' and inserts the ends approximately 1 centimeter inwardly upon the device. The surgeon secures the alternate embodiment of the device to each tendon with a transfixion stitch and then rolls each side of the device upwardly and around the two ends T, T' attaining the cylindrical like form shown in FIG. 11. The surgeon then extends a doubled suture through the outloops 6 and adjacent inloops 7 now adjacent to each other, in an alternating manner. The surgeon does this suture from both ends 2, 2a of the invention. With both ends sutured, the surgeon then pulls the sutures snug which closes the left side upon the right side of the invention generally above the tendon, not shown for clarity. The surgeon then takes another double suture and passes it through the outloops at each end and then the apertures in a generally spiral like manner. The surgeon pulls this other double suture and in doing so compresses the material of the device upon the tendon ends therein.

Figure 12:
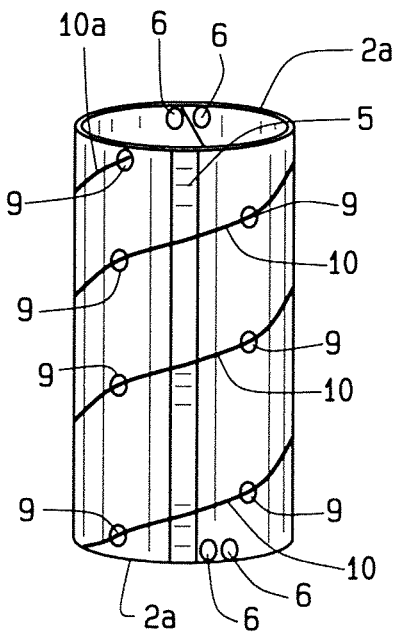
FIG. 12 provides a bottom view of the invention rolled.

FIG. 12 shows the alternate embodiment of the device upright but with the backer 2 in the foreground, that is, beneath a tendon repair. The other suture wraps about the device in a helical manner, thus facilitating compression of the tendon and improved healing thereof.

Figure 13:
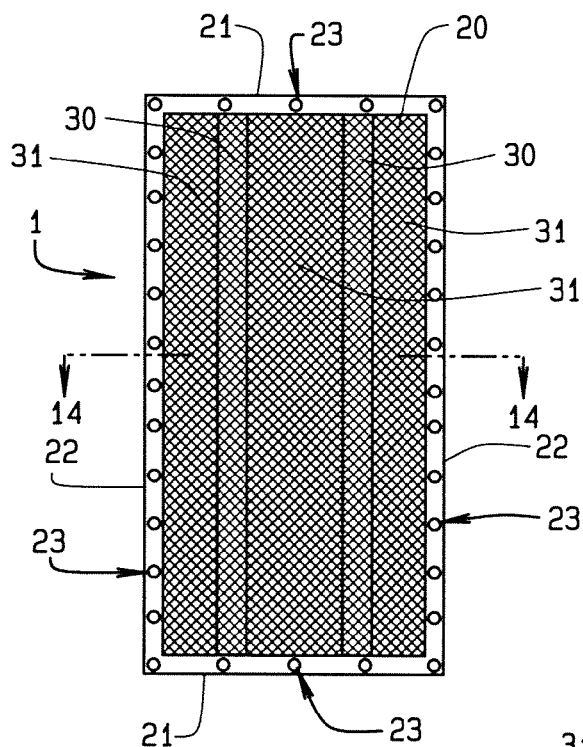
FIG. 13 shows a top view of an alternate embodiment of the present invention.

An alternate embodiment of the invention 1 appears in flat form from the top in FIG. 13. This alternate embodiment alters the mesh layer 2 so that the invention rolls into an ovoid cross section as later shown in FIG. 15. This alternate embodiment has a generally rectangular form with a mesh construction, as at 20. The invention has two mutually parallel and spaced apart lateral ends 21 and two mutually parallel and spaced apart longitudinal sides 22. The lateral ends being perpendicular to the longitudinal sides. Both the lateral ends and the longitudinal sides have a plurality of apertures 23 formed therein. Parallel to the sides, the mesh layer, as at 20, has two bands of thinner mesh as at 30. The two bands 30 are mutually parallel and extend for the length of the mesh. Between the two bands and outwardly from the bands, the mesh has a greater thickness, as at 31, typically shown as strips. The strips 31 are approximately double the thickness as the bands 30 but slightly less than the thickness of the edges of the sides 22. As before, the apertures 23, whether a puncture through reinforced edge or a grommet, receive sutures during installation of the invention upon a tendon. Approximate dimensions of the bands include 0.5 mm and of the strips includes 1.0 mm.

Figure 14:
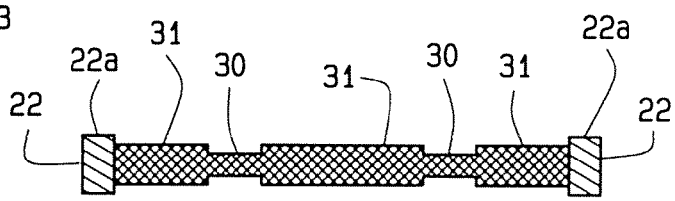
FIG. 14 describes a section view of the alternate embodiment of FIG. 13.

FIG. 14 provides a sectional view through the alternate embodiment of the mesh. The mesh has a generally rectangular cross section but upon closer inspection of this Figure, the mesh has two spaced apart sides 22. Each side has a thickness as at 22a. Inwardly from each side, the mesh 20 steps down in thickness slightly for the strips 31. The side has a smoothed transition to the adjacent strip. Inwardly from each strip, the mesh steps down again in thickness, approximately 50% for the bands 30. And inwardly from the bands, the mesh steps up in thickness back to the thickness of the strips 31. The mesh also has a smooth transition between the strips and the adjacent bands. The generally thinner bands permit the mesh to roll upwardly and inwardly and to attain and an ovoid cross section, similar to that of a tendon. The thinner bands permit the spaced apart bending of the mesh at the end of the major axis as at 25 of the ovoid shape, such as at the curved portions of the ovoid shape, while the thicker bands lessen the mesh bending at the ends of the minor axis as at 26, such as the flatter portions of the ovoid shape. The thicknesses of the bands and the strips cooperate and establish a mesh, as at 20, of differential rigidity that attains an ovoid cross section. The bands have a width of one half millimeter or multiple thereof and the strip has a width of one millimeter or multiple thereof.

Figure 15:
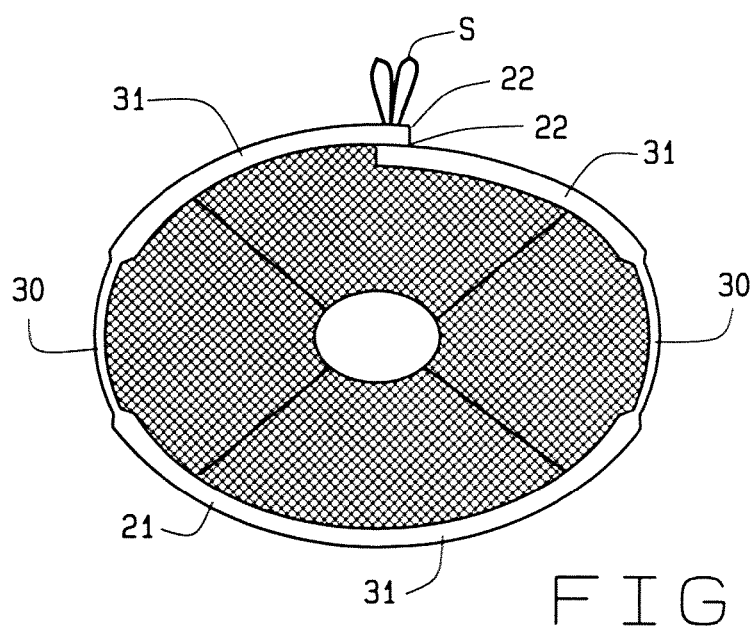
FIG. 15 shows an end view of the alternate embodiment of FIG. 13 when installed.

FIG. 15 provides an end view of an alternate embodiment of the invention previous shown in FIGS. 13, 14. In this view, the sides 22 are brought upwardly and inwardly by the surgeon to surround a tendon, not shown. The surgeon positions the sides 22 mutually adjacent in a butt joint, as shown, without an overlap. The surgeon then secures the sides with a suture as at S. The sutures secure the two thickened edges 22a of the mesh 20 spaced apart and opposite the centermost strip 31 so that the sutures and centermost strip define the ends of the minor axis 26 of the ovoid shape. Outwardly from the centermost strip 31, the mesh thins through the two bands 30 and the mesh rolls upwardly and inwardly utilizing its shape memory. The lesser thickness of the two bands allows the mesh to roll more tightly and transition to above the centermost strip towards the joint closed by the sutures as at S. The two bands are generally mutually spaced apart upon the ends of the minor axis 25 of the ovoid shape. The bands are somewhat perpendicular to the centermost strip 31 and the abutting sides 22 at the suture S. The ovoid shape of this alternate embodiment fits within the palmar/volar recesses established in digital and phalangeal joints.

Figure 16:
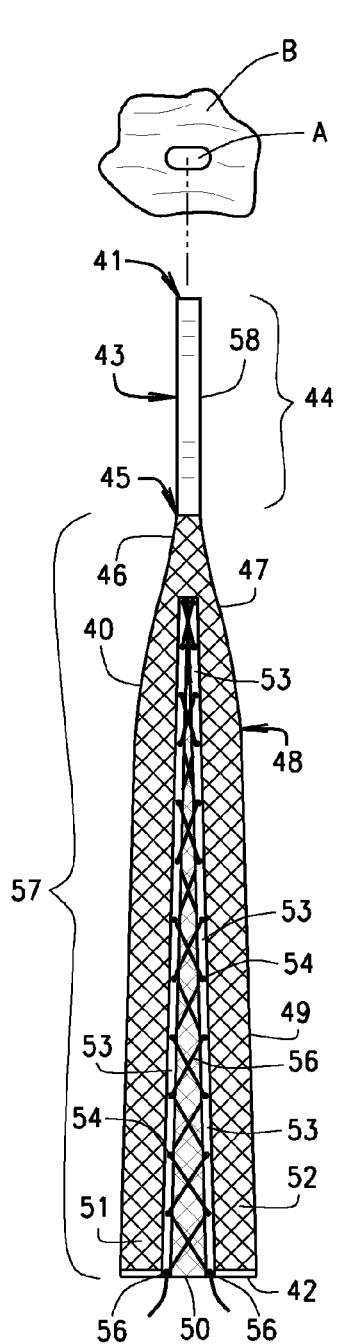
FIG. 16 provides a top view of the third alternate embodiment of the invention in the open position.

FIG. 16 shows a top view of a third alternate embodiment of the present invention. In the body of a patient, elongated tissue connects to other elongated tissue and elongated tissue also secures to bone and other solid parts of the body. The elongated tissue narrows in its shape and may pass through an aperture A, a recess, or a grove, in bone B as shown towards the top of FIG. 16. Going forward, distal refers to the direction towards the bone B and proximal refers to the direction away from the bone B and towards the elongated healing tissue. The present invention in this embodiment narrows to enter a natural aperture A in a bone B. The present invention seeks to replicate the natural connection of elongated tissue to a bone. This embodiment of the invention has a sheet of mesh, as at 40, generally of a frusto-conical shape with a fixed end 41 and an opposite free end 42. The fixed end 41 allows for the securement of the invention to the body using an anchor as is common in the art. The anchor can be a suture anchor which captures the fixed end in a positive grip. The free end has a greater width than the fixed end and receives the elongated tissue T for securement as later shown.

The invention has two major components: a proximal component 57 and a coaxial distal component 58. The proximal component includes the free end 42 and receives the elongated tissue and the distal component includes the fixed end 41. The proximal component has a generally conical shape with an open longitudinal slit 53 of an elongated tapered V shape which extends for the length of the proximal component.

The distal component has a preferred composition of suture material and has significantly smaller and narrower dimensions than the proximal component. The distal component has a firm attachment to a tapered terminal end of the proximal component through adhesion, welding, weaving, mechanical connection and the like as subsequently described. The distal component serves as an anchorage for the device so that a tendon or other elongated body tissue can have a firm anchoring or fixing to bone or other rigid tissue. The distal component forms its anchorage utilizing sutures, suture anchors, interference screws, and like means to provide secure, permanent fixation of the device and attached tendon or other elongated body tissue to bone. The invention's distal component 58 extends from the fixed end with a fixation element 43. The fixation element has a generally thin cross section, similar to that of a ribbon, and alternatively with an ovoid cross section to follow that of the tissue under repair. The fixation element is generally solid, or alternatively of braids, and resists the tensile loading foreseen for the tissue under repair with a factor of safety applied to the loadings. The fixation element has its length 44 that exceeds its width by at least a factor of two. Opposite the fixed end, the fixation element 43 has a joint 45 that receives a tip 46 of mesh material from the remainder of the invention, that is, the proximal component. The joint provides a continuous connection, whether mechanical, woven, adhesive, or welded, between the tip and the fixation element thus merging the distal component 58 to the proximal component 57.

The tip 46 provides the narrow portion of the proximal component that then widens along its length to the free end 42. The tip also serves as the beginning of the prime taper zone, as at 47, of the proximal component. The prime taper zone has an inverted, truncated rounded conical shape, here shown from the side. The prime taper zone has a length similar to that of the fixation element and a width that widens to at least twice the width of the fixation element. The prime taper zone has a curvature similar to that of a champagne flute proximate to its merging into a stem. The prime taper zone flattens its taper, that is, makes it closer to parallel to the length of the fixation element, as at 48. Where the prime taper zone flattens, at 48, the invention commences the second taper zone 49. The second taper zone widens from the merge with the prime taper zone 48 to the free end 42 of the proximal component. The widening of the second taper zone occurs more gradually than that of the prime taper zone. The second taper zone has its length at least 150% of the length of the prime taper zone. The length of the second taper zone provides for a secure grip along a length of elongated tissue T as later shown in FIG. 17. The second taper zone has a generally constant widening along its length. Alternatively, the prime taper zone and the second taper zone are replaced with a third taper zone having a conical shape with a constant taper for the entire proximal component. The present invention seeks to reproduce the natural shape of the elongated tissue and does not attain a cylindrical form.

Outwardly from the tip 46, the proximal component of the invention has mesh construction for the prime taper zone 47 and the second taper zone 49. Further, the invention has a slit 50 extending through the second taper zone 49 and into the prime taper zone 47, preferably to the vicinity of the tip 46. Containing the slit, the prime taper zone and the second taper zone of material of the invention have a left wing 51 and an opposite right wing 52. The left wing and the right wing represent two edges of mesh material formed into the frusto conical shape of the proximal component. Proximate the slit 50, the left wing and the right wing each have a hem 53 formed from a folded over longitudinal side. The hem on each wing extends from the free end to proximate the tip. The hem represents a reinforced edge and has a plurality of spaced holes 54 along its length. The holes receive at least one lace 55, often a suture, inserted therein in a pattern. An exemplary pattern includes the midpoint of the lace inserted into opposite holes 54 proximate the tip 46 and the lace is then crossed and inserted into the next outward pair of holes and the pattern repeats to the free end 42. This exemplary pattern of lacing through the holes 54 in the hems 53 draws the left wing to the right wing so that the invention compresses any elongated tissue placed therein. The lacing 55 terminates in its ends 56 here shown extending outwardly from the free end.

Figure 17:
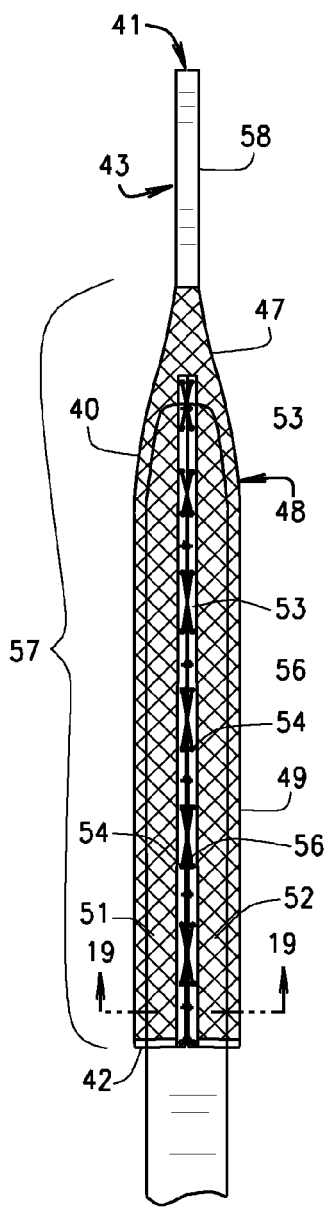
FIG. 17 shows a top view of the third alternate embodiment in the closed position.

FIG. 17 then shows the invention during its use. Following preparation of the elongated tissue, such as a tendon T, the surgeon inserts the tissue into the wide free end 42 of the proximal component 57. The surgeon advances the tissue through the second taper zone 49, past the taper flattening point as at 48, and into the prime taper zone 47. The prime taper zone has a shape that follows that of the end of the tissue for a snug fit. The surgeon may apply a temporary hold suture from the proximal component 57 near the free end. The surgeon then grasps the free ends of the lacing, as at 56, and pulls them gently. In doing so, the left wing 51 draws closer to the right wing 52 as the lacing 56 closes the hems 53 upon each other and the V shaped slit 50 closes. The surgeon pulls the lacing snug so that the hems 53 abut in a smooth manner to prevent abrasions and friction with adjacent tissues during healing.

Figure 18:
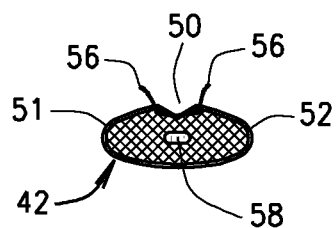
FIG. 18 shows an end view of the third alternate embodiment of the invention prior to closure.

Turning the invention on end, FIG. 18 shows the proximal component 57 from its free end 42 in the foreground with the distal component in the background, that is center of the figure. The free end 42 has a generally ovoid shape similar to that of the tissue T. The ovoid shape arises from the left wing 51 and the right wing 52 having complementary elliptical like shapes here shown on end view. The left wing and the right wing nearly approach but leave the V shape slit 50 between them, generally towards the top of this figure. The slit has lacing 56 as its boundaries and shows extensions of the lacing outwardly from the proximal component. The lacing is generally a flexible, slender, elongated material suitable for tensile loads and tying by a surgeon. Beneath the slit 50 and generally centered within the proximal component here shown, the invention has its distal component 58, more particularly the end view of the fixation element 43 appears. The fixation element has a flattened ovoid shape with two generally parallel surfaces oriented parallel to the width of the free end 42 and two rounded edges oriented similarly to the left wing and the right wing as at the free end.

Figure 19:
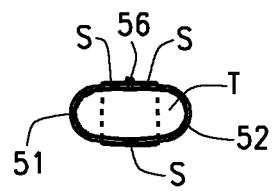
FIG. 19 shows an end view of the third alternate embodiment installed upon elongated tissue.

Following FIG. 17's description, FIG. 19 shows a sectional view of the invention installed upon tissue T. Upon pulling the lacing 56, the surgeon tightens the proximal component 57 upon the tissue T. The surgeon advances the left wing 51 to the right wing 52 and closes the slit 53 as the wings abut upon their hems 53. The surgeon then pulls the lacing 56 snug and ties it off using select knots. But if needed in the surgeon's judgment, he then applies a transfixion stitch as at S or an additional suture through the mesh of the proximal component 57 and into the tissue, such as a tendon T. These two sutures through the tissue mechanically connect the proximal component of this embodiment of the invention to the tissue.

Figure 20:
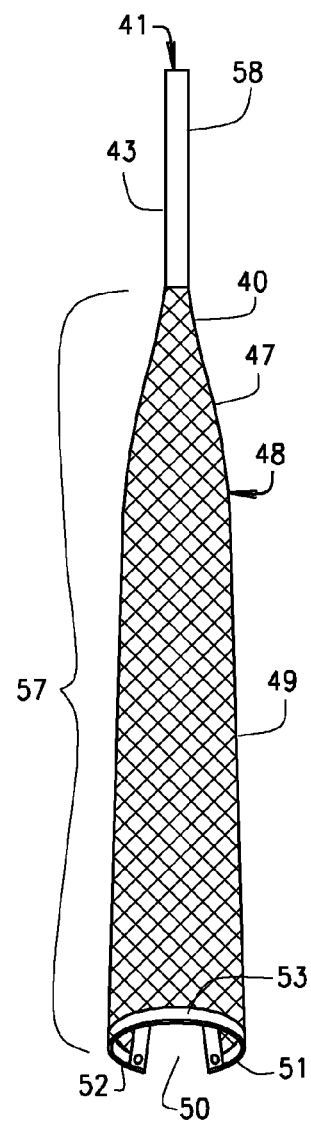
FIG. 20 illustrates a bottom view of the third alternate embodiment in the open position.

FIGS. 16, 17 show the invention from a top view with FIG. 16 showing the invention open and FIG. 17 showing the invention closed upon tissue. The slit 50 represents a gap between the left wing and the right wing. The left wing and the ring wing continue around the proximal component as continuous material. FIG. 20 shows a bottom view of the invention, that is, opposite FIGS. 16, 17. This view has the left wing and the right wing in the background and the reminder of the proximal component in the foreground. The proximal component has its material of construction continuous with the left wing and the ring wing so that no seam appears. The proximal component has the second taper zone 49 that merges as at 48 with the prime taper zone 47 to the distal component 58 with its fixation element 43.

Figure 21:
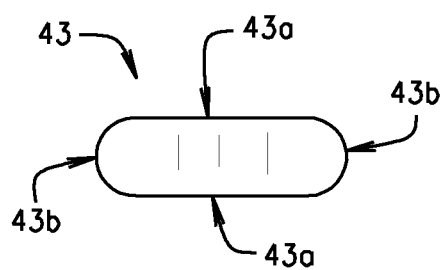
FIG. 21 describes another end view of a further alternate embodiment.

As previously described, the distal component has a fixation element 43 generally of ovoid cross section shown in FIG. 21. The fixation element has a ribbon like form with a length greater than the width of its cross section and a thin depth in proportion to its width. The fixation element has two space apart parallel surfaces at 43a connected by two spaced apart curved ends as at 43b. This cross section follows that previously shown in FIG. 18. The two surfaces 43a have an orientation parallel to that of the hems 53 when closed. This orientation allows the fixation element to travel smoothly upon any surfaces encountered in the aperture A of the bone B or other rigid tissue anchor point. The two surfaces have a width that exceeds the thickness shown by the two curved ends.

Figure 22:
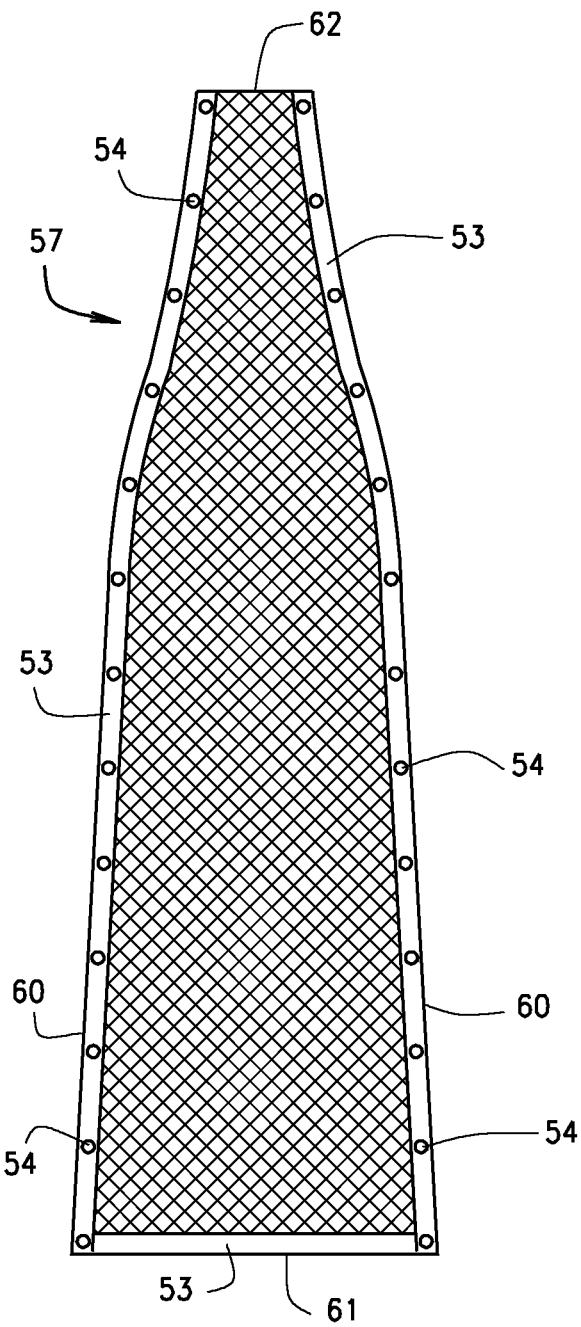
FIG. 22 shows a plan view of the further alternate embodiment in flat form; and, FIG. 23 shows an alternate embodiment of the invention including multiple "tails" for the distal component.

FIG. 22 shows the proximal component in flat form, generally before merging with the distal component. The proximal component 57 is composed of a sheet of mesh material generally having an isosceles trapezoidal shape when flat with two longitudinal sides 60, and a first lateral end 61 and a second lateral end 62 both at an angle to the longitudinal sides. The sheet mesh material allows for passage of fluids and gases present in healing tissue. The first lateral end and the second lateral end of the trapezoid are mutually parallel and spaced apart. The two longitudinal sides of the trapezoid are skewed and attain a mutually included angle. The wider end of the proximal component, that is, the first lateral end 61 and the two sides 60 also fold inwardly which presents smooth surfaces, or hems 53, upon which the healing elongated tissue, such as a tendon, rests and where the sheet mutually joins upon enwrapping the healing tissue as previously shown in FIGS. 16, 17. The hems on the sides 60 have a pattern of holes 54 spaced along each of them.

When assembled, this terminal tissue attachment and repair device attains a somewhat conical shape and tapered open V shaped slit with the narrow portion of the slit oriented distally and the wider end of the conical shape being oriented proximally as shown in FIGS. 16, 17, 20. The two longitudinal sides 53 of the slit 50 roll inwardly as the left wing and the right wing and present their plurality of holes 54 to receive suture material for lacing, as at 56, the slit closed. The distal, terminal end of the proximal component, that is, the second lateral end 62 rolls to tight mutual contact of both sides and then merges as at 46 to the joint 45 to the distal component 58 for use as an anchor.

Figure 23:
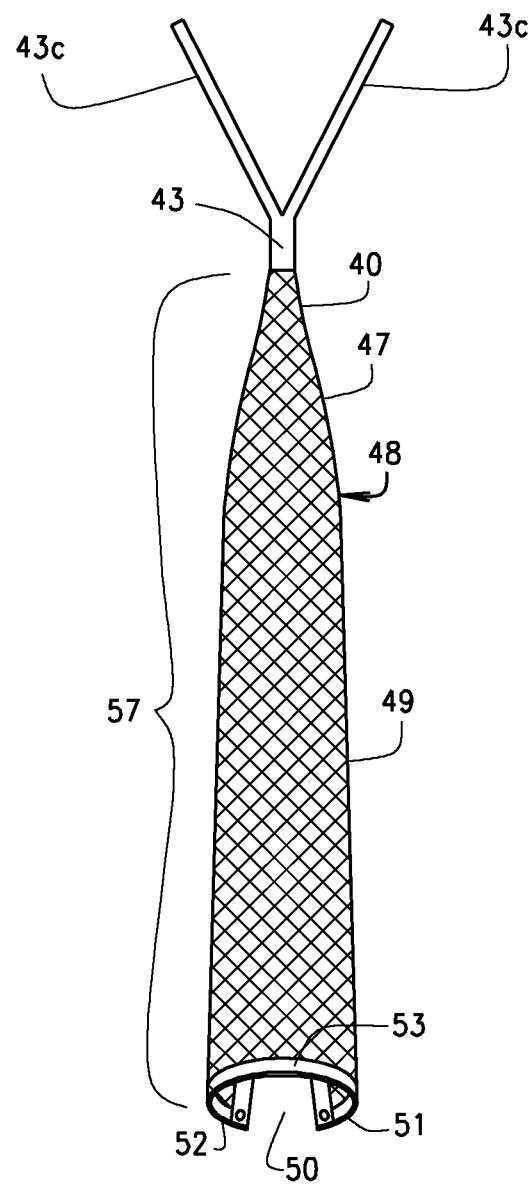

And, FIG. 23 provides an alternate embodiment of the invention. This figure shows a bottom view of the invention related to FIG. 20. This view has its left wing and right wing in the background and the reminder of the proximal component in the foreground. The proximal component has its material of construction continuous with the left wing and the ring wing so that no seam appears. The proximal component has the second taper zone 49 that merges as at 48 with the prime taper zone 47 to the distal component 58 with its fixation element 43. The fixation element then divides into two filaments, 43c, or strands, or ribbons, or tails as shown. The filaments mutually cooperate and attain a cross sectional shape similar to that of a natural tendon or other tissue. The cross section shape approximates an ovoid cross section. The fixation element also has its shaping and construction to receive an anchor. Though this figure shows two filaments, the Applicant foresees additional numbers of filament as components of the fixation element.

From the aforementioned description, a terminal tissue attachment and repair device has been described. The terminal tissue attachment and repair device is uniquely capable of capturing an end of severed tissue, or tendon, and compressing that end as a surgeon pulls the lacing or suture of the invention from one end only. The terminal tissue attachment and repair device further wraps the repair site and withstands the axial forces upon application of customary loads by the elongated tissue. The terminal tissue attachment and repair device and its various components may be manufactured from many materials, including but not limited to, polymers, non-resorbable suture material such as nylon, congealed 7.0 nylon, polypropylene, resorbable suture material such as polygalan, Vicryl®, or polydioxane, PDS, polyvinyl chloride, high density polyethylene, polypropylene, select plant materials, such as wood or corn derived plastics, ferrous and non-ferrous metals, their alloys, and composites.

Various aspects of the illustrative embodiments have been described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations have been set forth in order to provide a thorough understanding of the illustrative embodiments. However, it will be apparent to one skilled in the art that the present invention may be practiced without the specific details. In other instances, well known features are omitted or simplified in order not to obscure the illustrative embodiments.

Various operations have been described as multiple discrete operations, in a manner that is most helpful in understanding the present invention, however, the order of description should not be construed as to imply that these operations are necessarily order dependent. In particular, these operations need not be performed in the order of presentation.

Moreover, in the specification and the following claims, the terms "first," "second," "third" and the like—when they appear—are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to ascertain the nature of the technical disclosure. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

I claim:

1. A device for attaching a slender flexible elongated tissue of a patient to a distal bony insertion or a fixed skeletal point, comprising:
   a proximal component having a mesh construction, a tip and an opposite free end, a length from said tip to said free end, a left wing and an opposite right wing, said left wing and said right wing spanning from said free end to said tip, a slit spacing apart said left wing from said right wing, each of said left wing and said right wing having a hem thereon and each of said hems upon said left wing and said right wing having a plurality of holes spaced along them, said free end having a hem thereon, a suture lacing through the plurality of holes in said hems of said left wing and said right wing, said suture having its free ends extending outwardly from said free end, said proximal component attaining a frusto conical form upon rolling said left wing proximate said right wing;
   a distal component having a slender, elongated fixation element of lesser width than said proximal component composed of at least one slender filament, said fixation element having a joint connecting said distal component to said tip of said proximal component and an opposite fixed end, said fixed end adapted to anchor said device to a distal bony insertion;
   said device having a first position wherein said slit remains open wherein said hems of said left wing and said right wing remain spaced apart in a V shape loosely spanned by said suture; and,
   said device having a second position following a user pulling said free ends of said suture, said second position thus having said left wing adjoin to said right wing and said hems mutually abut, and a user secures said free ends of said suture to said free end of said proximal component;
   wherein said device is adapted to compress the flexible elongated tissue circumferentially along the length of said proximal component and said proximal component and is adapted to close from said free end only.

2. The device for attaching a slender flexible elongated tissue of a patient of claim 1 further comprising:
   said proximal component tapering from said free end to said tip.

3. The device for attaching a slender flexible elongated tissue of a patient of claim 2 further comprising:
   said proximal component having a second taper zone tapering from said free end to a merge at a rate and a prime taper zone tapering from said merge to said tip at a greater rate than said second taper zone.

4. The device for attaching a slender flexible elongated tissue of a patient of claim 3 further comprising:
   said proximal component having a second taper zone tapering from said free end to a merge at a rate and a prime taper zone curving and narrowing in width from said merge to said tip at a variably increasing rate.

5. The device for attaching a slender flexible elongated tissue of a patient of claim 1 further comprising:
   said proximal component tapering from said free end to said tip at a constant rate.

6. The device for attaching a slender flexible elongated tissue of a patient of claim 1 further comprising:
   said proximal component being a planar sheet when in flat form, said sheet having a generally trapezoidal form, a first lateral end and a second lateral end being mutually parallel and spaced apart, two spaced apart longitudinal sides mutually inclined inwardly, an inner surface and an opposite outer surface, said inner surface adapted to contact the tissue;
   said first lateral end forming said tip upon rolling of said sheet and said second lateral end forming said free end upon rolling of said sheet;
   said two spaced apart longitudinal sides forming said left wing and said right wing respectively and having said slit between said left wing and said ring wing upon rolling of said sheet.

7. The device for attaching a slender flexible elongated tissue of a patient of claim 1 further comprising:
   said distal component having a ribbon like form and an ovoid cross section and said fixed end being adapted to receive an anchor;
   said ovoid cross section being adapted to provide direct contact to the elongated tissue;
   said proximal component adapted to gather and to compress the tissue;
   said device adapted to attach to the tissue and to secure the tissue to a distal bony insertion of a patient; and
   said device attaining a shape similar to that of the tissue.

8. The device for attaching a slender flexible elongated tissue of a patient of claim 1 further comprising:
   said proximal component having an inner surface and an opposite outer surface, said inner surface adapted to contact the tissue, adapted to bind to the tissue for an intimate connection of said device to the tissue, and adapted to stimulate grown of the tissue into said device.

9. The device for attaching a slender flexible elongated tissue of a patient of claim 8 further comprising:
   said inner surface binding to the tissue by one of mechanical means, high coefficient of friction material, roughened surface, adhesive, and cohesive.

10. A surgical repair device suitable for single handed closure by a surgeon, said device attaching a slender flexible elongated tissue of a patient to a distal bony insertion or a fixed skeletal point, comprising:
    a distal component having a solid construction, at least one elongated fixation element having a joint and an opposite fixed end, said fixed end adapted to anchor said device to a distal bony insertion;
    a proximal component having a mesh construction of greater width than said distal component, a tip and an opposite free end, a length from said tip to said free end, said tip merging said proximal component to said joint of said distal component, a left wing and an opposite right wing, said left wing and said right wing spanning from said free end to said tip, a slit spacing apart said left wing from said right wing, each of said left wing and said right wing having a hem thereon and each of said hems upon said left wing and said right wing having a plurality of holes spaced along them, said free end having a hem thereon, a suture lacing through the plurality of holes in said hems of said left wing and said right wing, said suture having its free ends extending outwardly from said free end, said proximal component attaining a frusto conical form upon bringing said left wing proximate said right wing;

said device having a first position wherein said slit remains open wherein said hems of said left wing and said right wing remain spaced apart in a V shape loosely spanned by said suture; and, said device having a second position following a user pulling said free ends of said suture, said second position thus having said left wing adjoin to said right wing and said hems mutually abut, and a user secures said free ends of said suture to said free end of said proximal component;

wherein said device is adapted to compress the flexible elongated tissue circumferentially along the length of said proximal component, to approach similarity to normal tissue anatomy, and said proximal component is adapted to close from said free end only.

11. The single handed closure surgical repair device of claim 10 further comprising:

said proximal component being a planar sheet when in flat form, said sheet having a generally trapezoidal form, a first lateral end and a second lateral end being mutually parallel and spaced apart, two spaced apart longitudinal sides mutually inclined inwardly, an inner surface and an opposite outer surface, said inner surface adapted to contact the tissue;

said first lateral end forming said tip upon rolling of said sheet and said second lateral end forming said free end upon rolling of said sheet;

said two spaced apart longitudinal sides forming said left wing and said right wing respectively and having said slit between said left wing and said ring wing upon rolling of said sheet.

12. The single handed closure surgical repair device of claim 11 further comprising:

said proximal component tapering from said free end to said tip.

13. The single handed closure surgical repair device of claim 12 further comprising:

said proximal component having a second taper zone tapering from said free end to a merge at a rate and a prime taper zone tapering from said merge to said tip at a greater rate than said second taper zone.

14. The single handed closure surgical repair device of claim 13 further comprising:

said proximal component having a second taper zone tapering from said free end to a merge at a rate and a prime taper zone curving and narrowing in width from said merge to said tip at a variably increasing rate.

15. The single handed closure surgical repair device of claim 12 wherein said proximal component tapers from said free end to said tip at a constant rate.

16. The single handed closure surgical repair device of claim 11 further comprising:

said distal component having at least one filament having an ovoid cross section and said fixed end being adapted to receive an anchor;

said proximal component adapted to gather and to compress the tissue;

said proximal component having an inner surface and an opposite outer surface, said inner surface contacting the tissue, said inner surface being adapted to bind to the tissue for an intimate connection of said device to the tissue and being adapted to stimulate growth of the contained tissue into said device;

said device adapted to attach to the tissue and to secure the tissue to a distal bony insertion of a patient and said device attaining a shape similar to that of the tissue.

17. A surgical repair device which secures a terminal end of elongated human tissue to a distal bony insertion or a fixed skeletal point during healing of the tissue, said surgical repair device comprising:

a sheet of material having a mesh like construction, a first lateral end and an opposite second lateral end, and two spaced apart longitudinal sides further comprising a left wing and an opposite right wing, a plurality of holes spaced along each of said sides;

said device attaining a frusto-conical form upon rolling said left wing proximate said right wing and said first lateral end including a mutual joint of said left wing to said right wing;

a proximal component forming of said left wing and said right wing spaced apart by a V shaped slit extending from said second lateral end towards said mutual joint, said proximal component having a length from said mutual joint to said second lateral end and a width at said second lateral end;

a distal component extending from said second lateral, having a slender, elongated fixation element of lesser width than said proximal component, said fixation element having a joint connecting said distal component to said mutual joint of said proximal component and an opposite fixed end, said fixed end adapted to anchor said device to a distal bony insertion;

a suture lacing through said plurality of holes in said first side and said second side, said suture extending from said second lateral end towards said mutual joint, said suture having free ends extending outwardly from said second end;

said device having a first position wherein said left wing and said right wing form a V shaped slit with said mutual joint defining a vertex of the V shape and said suture loosely spanning said slit from said left wing to said right wing; and, said device having a second position following a user pulling said free ends of said suture, said second position having said left wing and said right wing mutually abut, and a user securing said free ends to said second lateral end;

wherein said device is adapted to compress the elongated tissue circumferentially upon the length of said proximal component and is adapted to simulate normal anatomic shape of the elongated tissue;

said suture allowing for closure of said device into its second position from said second lateral end; and, whereby said device being in said second position, a user secures said device to the elongated tissue using transverse transfixion sutures placed through said device and the elongated tissue.

18. The surgical repair device for elongated tissue attachment of claim 17 further comprising:

said proximal component having a second taper zone tapering from said second lateral end to a merge at a rate and a prime taper zone tapering from said merge to said mutual joint at a greater rate than said second taper zone.

19. The surgical repair device for elongated tissue attachment of claim 17 further comprising:

said proximal component having a second taper zone tapering from said second lateral end to a merge at a rate and a prime taper zone curving and narrowing in width from said merge to said mutual joint at a variably increasing rate.

20. The surgical repair device for elongated tissue attachment of claim 17 further comprising:

said distal component having at least one filament having an ovoid cross section and said fixed end being adapted to suture directly or to receive an anchor.

* * * * *